(12) United States Patent
Rocque et al.

(10) Patent No.: US 10,074,184 B2
(45) Date of Patent: Sep. 11, 2018

(54) OCCUPANCY DETECTION

(71) Applicant: KONINKLIJKE PHILIPS N.V., Eindhoven (NL)

(72) Inventors: Mukul Julius Rocque, Eindhoven (NL); Ihor Olehovych Kirenko, Veldhoven (NL)

(73) Assignee: KONIKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/508,142

(22) PCT Filed: Aug. 10, 2016

(86) PCT No.: PCT/EP2016/069073
§ 371 (c)(1),
(2) Date: Mar. 2, 2017

(87) PCT Pub. No.: WO2017/025571
PCT Pub. Date: Feb. 16, 2017

(65) Prior Publication Data
US 2018/0158192 A1  Jun. 7, 2018

(30) Foreign Application Priority Data
Aug. 10, 2015  (EP) ..................................... 15180328

(51) Int. Cl.
*G06T 7/13* (2017.01)
*G06T 7/174* (2017.01)
(Continued)

(52) U.S. Cl.
CPC .............. *G06T 7/13* (2017.01); *A61B 5/0075* (2013.01); *A61B 5/0077* (2013.01);
(Continued)

(58) Field of Classification Search
CPC ......... G06T 7/13; G06T 7/174; A61B 5/0075; A61B 5/0077; A61B 5/1128;
(Continued)

(56) References Cited

U.S. PATENT DOCUMENTS 7,200,246 B2 * 4/2007 Cofer ..................... F16P 3/142
348/152
7,541,934 B2  6/2009 Fredriksson
(Continued)

FOREIGN PATENT DOCUMENTS

| EP | 2161695 | 3/2010 |
|----|---------|--------|
| WO | 2007/020666 | 2/2007 |
| WO | 2009075559 | 6/2009 |

OTHER PUBLICATIONS

Debard, et al., "Camera-based fall detection on real world data", Outdoor and Large-Scale Real-World Scene Analysis, vol. 7474 of the series Lecture Notes in Computer Science pp. 356-375, 2012.

*Primary Examiner* — Jay Au Patel
*Assistant Examiner* — Irfan Habib

(57) ABSTRACT

There is provided an apparatus for detecting when a subject has exited an item of furniture which has an upper side for supporting a subject and an underside opposite to the upper side, and comprises an overhanging component that extends from the underside toward a surface on which the item of furniture is resting. The apparatus comprises a light source to illuminate an edge-feature associated with a distal edge of the overhanging component, to create a shadow of the edge-feature on a region of the surface. The apparatus further comprises a camera arranged to capture sequential images of the region of the surface; and a processing unit. The processing unit is arranged to receive the images; detect an edge of the shadow in each of the received images, detect, in the received images, the appearance of a feature contiguous with the shadow edge; monitor how a detected feature
(Continued)

changes over a time period; determine whether a change to the detected feature satisfies at least one predefined criterion for a subject exit event; and output a signal based on the determining.

15 Claims, 6 Drawing Sheets

(51) Int. Cl.
| | | |
|---|---|---|
| *G06K 9/00* | (2006.01) | |
| *H04N 5/225* | (2006.01) | |
| *H04N 5/33* | (2006.01) | |
| *H04N 5/232* | (2006.01) | |
| *A61B 5/00* | (2006.01) | |
| *A61B 5/11* | (2006.01) | |
| *G08B 21/04* | (2006.01) | |

(52) U.S. Cl.
CPC .......... *A61B 5/1115* (2013.01); *A61B 5/1128* (2013.01); *A61B 5/6891* (2013.01); *G06K 9/00771* (2013.01); *G06T 7/174* (2017.01); *H04N 5/2256* (2013.01); *H04N 5/23229* (2013.01); *H04N 5/332* (2013.01); *G08B 21/0446* (2013.01); *G08B 21/0461* (2013.01)

(58) Field of Classification Search
CPC .. H04N 5/2256; H04N 5/332; G08B 21/0446; G08B 21/0461
See application file for complete search history.

(56) References Cited

U.S. PATENT DOCUMENTS

| | | | | |
|---|---|---|---|---|
| 9,171,213 | B2* | 10/2015 | Bulan | G06K 9/00785 |
| 9,672,434 | B2* | 6/2017 | Wu | G06K 9/00812 |
| 9,858,816 | B2* | 1/2018 | Cook | G08G 1/14 |
| 2005/0122397 | A1* | 6/2005 | Henson | H04N 7/181 |
| | | | | 348/143 |
| 2007/0127774 | A1* | 6/2007 | Zhang | G06K 9/00771 |
| | | | | 382/103 |
| 2009/0278934 | A1 | 11/2009 | Ecker | |
| 2010/0328443 | A1 | 12/2010 | Lynam | |
| 2011/0043630 | A1* | 2/2011 | McClure | A61B 5/1116 |
| | | | | 348/143 |
| 2014/0240479 | A1* | 8/2014 | Yasukawa | G06K 9/00342 |
| | | | | 348/77 |
| 2014/0253710 | A1 | 9/2014 | Yasukawa | |
| 2014/0267663 | A1* | 9/2014 | Yasukawa | H04N 7/18 |
| | | | | 348/77 |
| 2014/0267774 | A1* | 9/2014 | Holz | G01S 3/7864 |
| | | | | 348/169 |
| 2014/0368652 | A1* | 12/2014 | Wang | G06K 9/00771 |
| | | | | 348/148 |
| 2014/0375804 | A1* | 12/2014 | Bulan | H04N 7/18 |
| | | | | 348/148 |
| 2015/0086071 | A1* | 3/2015 | Wu | G06T 15/205 |
| | | | | 382/103 |
| 2017/0042340 | A1* | 2/2017 | Chacon | A61G 5/14 |
| 2017/0109481 | A1* | 4/2017 | Johnson | G06F 19/327 |
| 2017/0115019 | A1* | 4/2017 | Desmet | F24F 2110/20 |
| 2017/0331899 | A1* | 11/2017 | Binder | H04L 67/12 |

* cited by examiner

OCCUPANCY DETECTION

CROSS REFERENCE TO RELATED APPLICATIONS

This application is the U.S. National Phase application under 35 U.S.C. § 371 of International Application No. PCT/EP2016/069073, filed Aug. 10, 2016, published as WO2017/025571 on Feb. 16, 2017 which claims the benefit of European Patent Application Number 15180328.5 filed Aug. 10, 2015. These applications are hereby incorporated by reference herein.

TECHNICAL FIELD OF THE INVENTION

The invention relates to an apparatus, system and method for detecting when a subject has exited an item of furniture.

BACKGROUND TO THE INVENTION

Detecting the movement and/or position of a subject is important in several healthcare applications. For example, it is often desired to prevent patients in hospital beds from moving in certain ways. As a result of medications, impaired memory, old age and/or other disabilities, patients who attempt to leave their beds without assistance often fall and injure themselves. Unassisted movement of a patient can also lead to medical devices attached to that patient becoming dislodged and ceasing to function properly.

However; the monitoring of patients who should not get out of bed without clinical assistance can place a significant burden on hospital staff.

Many current methods used for bed occupancy detection utilize a camera directed at the bed. In some examples a person (e.g. a medical professional) must constantly monitor the image feed from the camera. In other examples, such as the system described in US 2009/0278934, automated image analysis is used to detect bed exit events, but this requires complicated algorithms for detecting bed boundaries and classifying movements of the subject. Such algorithms can be confused by movements other than that of the subject (e.g. a blanket falling off the bed), leading to false alarms being raised when the subject is not attempting to exit the bed. Many such algorithms also require significant computational resource, since they continually estimate the position and/or motion of a monitored subject. Also, automated camera-based systems require recalibrating each time the relative position of the camera and the bed changes, and become unreliable if such recalibrations are not performed. An additional issue is the privacy of the monitored subject. It can be difficult to ensure that privacy is maintained when a monitoring system requires an image of the subject to be continually recorded.

Document US 2014/240479 relates to an information processing apparatus including an image acquisition unit to acquire images of a target person being observed and a target object being used as a reference for determining the behavior of the target person. The apparatus further comprises a moving object detection unit to detect from the images motion occurring in a given area, and a behavior estimation unit to estimate a behavior of the target person being observed with respect to the target object based on their positional relationship.

There is therefore a need for an automated monitoring system which is reliable, unobtrusive and computationally efficient, and which is able to monitor subjects occupying hospital beds and/or other items of furniture to detect when a subject attempts to leave a bed or other item of furniture.

SUMMARY OF THE INVENTION

According to a first aspect of the invention, there is provided an apparatus for detecting when a subject has exited an item of furniture. The item of furniture has an upper side for supporting a subject and an underside opposite to the upper side, and comprises an overhanging component that extends from the underside toward a surface on which the item of furniture is resting. The overhanging component comprises a proximal edge and a distal edge opposite to the proximal edge, the distal edge being farther from the underside than the proximal edge. The apparatus comprises a light source for use underneath an item of furniture, and the light source is arranged to illuminate an edge-feature associated with the distal edge of the overhanging component of the item of furniture such that a shadow of the edge-feature is created on a region of the surface. The apparatus further comprises at least one camera arranged to capture sequential images of the region of the surface; and a processing unit. The processing unit is arranged to: receive the images from the camera; detect an edge of the shadow in each of the received images, detect, in the received images, the appearance of a feature contiguous with the shadow edge; monitor how a detected feature changes over a time period; determine whether a change to the detected feature over the time period satisfies at least one predefined criterion for a subject exit event; and output a signal based on the determining.

In some embodiments the processing unit is arranged to detect the appearance of a feature contiguous with the shadow edge by: comparing a first image acquired at a first time, to a second image acquired at a second, later, time; and if a feature contiguous with the shadow edge is present in the second image but is not present in the first image, determine that a feature has appeared contiguous with the shadow edge.

In some embodiments the processing unit is arranged to monitor changes to a detected feature over a time period by: determining a first value for a property of the feature in a first image acquired at a first time; determining a second value for the property of the feature in a second image acquired at a second, later, time; and comparing the second value to the first value. In some such embodiments the property of the feature is any one of: size of the feature, shape of the feature, location of the feature; extension of the feature perpendicular to the shadow edge.

In some embodiments the processing unit is arranged to monitor changes to a detected feature over a time period by determining a rate of change of the detected feature over the time period, based on the first value, the second value, the acquisition time of the first image, and the acquisition time of the second image.

In some embodiments the processing unit is arranged to monitor changes to a detected feature over a time period by determining a direction of motion of the detected feature over the time period; and wherein the at least one predefined criterion for a subject exit event comprises a condition relating to a direction of motion of a detected feature. In some such embodiments the predefined criterion for a subject exit event is defined such that motion of a detected feature in a direction toward the shadow edge during the time period will be determined by the processing unit to satisfy the predefined criterion and motion of a detected feature in a direction away from the shadow edge will be determined by the processing unit not to satisfy the predefined criterion.

In some embodiments the apparatus is additionally for detecting when a subject has entered an item of furniture and the processing unit is further arranged to determine whether a change to the detected feature over the time period satisfies at least one predefined criterion for a subject entry event; and wherein the predefined criterion for a subject entry event is defined such that motion of a detected feature over the time period in a direction toward the shadow edge will be determined by the processing unit not to satisfy the predefined criterion.

In some embodiments the apparatus further comprises an additional light source for use underneath an item of furniture, wherein the item of furniture comprises an additional overhanging component that extends from the underside toward the surface on which the item of furniture is resting, wherein the additional overhanging component comprises a proximal edge and a distal edge opposite to the proximal edge, wherein the distal edge is farther from the underside than the proximal edge. In some embodiments the light source and the additional light source are both for use underneath the same item of furniture. In some such embodiments the light source is arranged to illuminate a first edge-feature associated with the distal edge of the overhanging component of the item of furniture such that first a shadow is created on a first region of the surface and the additional light source is arranged to illuminate a second edge-feature associated with the distal edge of the additional overhanging component of the item of furniture such that a second shadow is created on a second region of the surface; the first region being adjacent a first side of the item of furniture, and the second region being adjacent a second, different, side of the item of furniture. In some embodiments the at least one camera is arranged to capture sequential images, each of which includes the first region and the second region. In some embodiments the processing unit is arranged to: detect an edge of the shadow in each of the received images by detecting an edge of the first shadow and an edge of the second shadow in each of the received images, and detect, in the received images, the appearance of a feature contiguous with the shadow edge by detecting the appearance of a feature contiguous with the first shadow edge and detecting the appearance of a feature contiguous with the second shadow edge.

In some embodiments the light source is arranged to emit near-infrared light and the at least one camera is arranged to detect near-infrared light.

In some embodiments the light source is arranged such that substantially all of the light emitted by the light source has a wavelength in a predefined range. In some embodiments the least one camera comprises an optical filter arranged to permit the passage of light having a wavelength in the predefined range and to block the passage of light having a wavelength outside of the predefined range.

There is also provided, according to a second aspect of the invention, a system for detecting when a subject has exited an item of furniture. The system comprises an item of furniture having an upper side for supporting a subject and an underside opposite to the upper side and comprising an overhanging component that extends from the underside toward a surface on which the item of furniture is resting, wherein the overhanging component comprises a proximal edge and a distal edge opposite to the proximal edge, the distal edge being farther from the underside than the proximal edge, the item of furniture further having, an edge-feature associated with the distal edge of the overhanging component. The system further comprises a light source arranged to illuminate the edge-feature associated with the distal edge of the overhanging component of the item of furniture such that a shadow of the edge-feature is created on a region of the surface. The system further comprises a camera arranged to capture sequential images of the region of the surface; and a processing unit. The processing unit is arranged to: receive the images from the camera; detect an edge of the shadow of the edge-feature in each of the received images, detect, in the received images, the appearance of a feature contiguous with the shadow edge; monitor how a detected feature changes over a time period; determine whether a change to the detected feature over the time period satisfies at least one predefined criterion for a subject exit event; and output a signal based on the determining.

In some embodiments the overhanging component is comprised in an edge member removably attached to the item of furniture. In some such embodiments the edge member comprises a linear protrusion which, when attached to the item of furniture, extends from the underside of the item of furniture toward the surface on which the item of furniture is resting.

There is also provided, according to a third aspect of the invention, a method for detecting when a subject has exited an item of furniture, the item of furniture having an upper side for supporting a subject and an underside opposite to the upper side and comprising an overhanging component that extends from the underside toward a surface on which the item of furniture is resting, wherein the overhanging component comprises a proximal edge and a distal edge opposite to the proximal edge, the distal edge being farther from the underside than the proximal edge. The method comprises:

receiving sequential images of a region of the surface, each of the images including a shadow cast by an edge-feature associated with the distal edge of the overhanging component of the item of furniture;

detecting an edge of the shadow in each of the received images, detecting, in the received images, the appearance of a feature contiguous with the shadow edge;

monitoring how a detected feature changes over a time period;

determining whether a change to the detected feature over the time period satisfies at least one predefined criterion for a subject exit event; and outputting a signal based on the determining.

Thus, embodiments of the invention advantageously provide a system which can reliably and unobtrusively monitor movements of a subject occupying an item of furniture, whilst using considerably less computational resource than conventional camera-based monitoring systems. In this manner bed (or other furniture) exit events can be detected automatically, which can considerably reduce the monitoring burden on medical staff.

BRIEF DESCRIPTION OF THE DRAWINGS

For a better understanding of the invention, and to show more clearly how it may be carried into effect, reference will now be made, by way of example only, to the accompanying drawings, in which:

FIG. 2b is a plan view of the arrangement of FIG. 2a;

FIG. 4b is a plan view of the scenario of FIG. 4a;

DETAILED DESCRIPTION OF THE PREFERRED EMBODIMENTS

Figure 1:
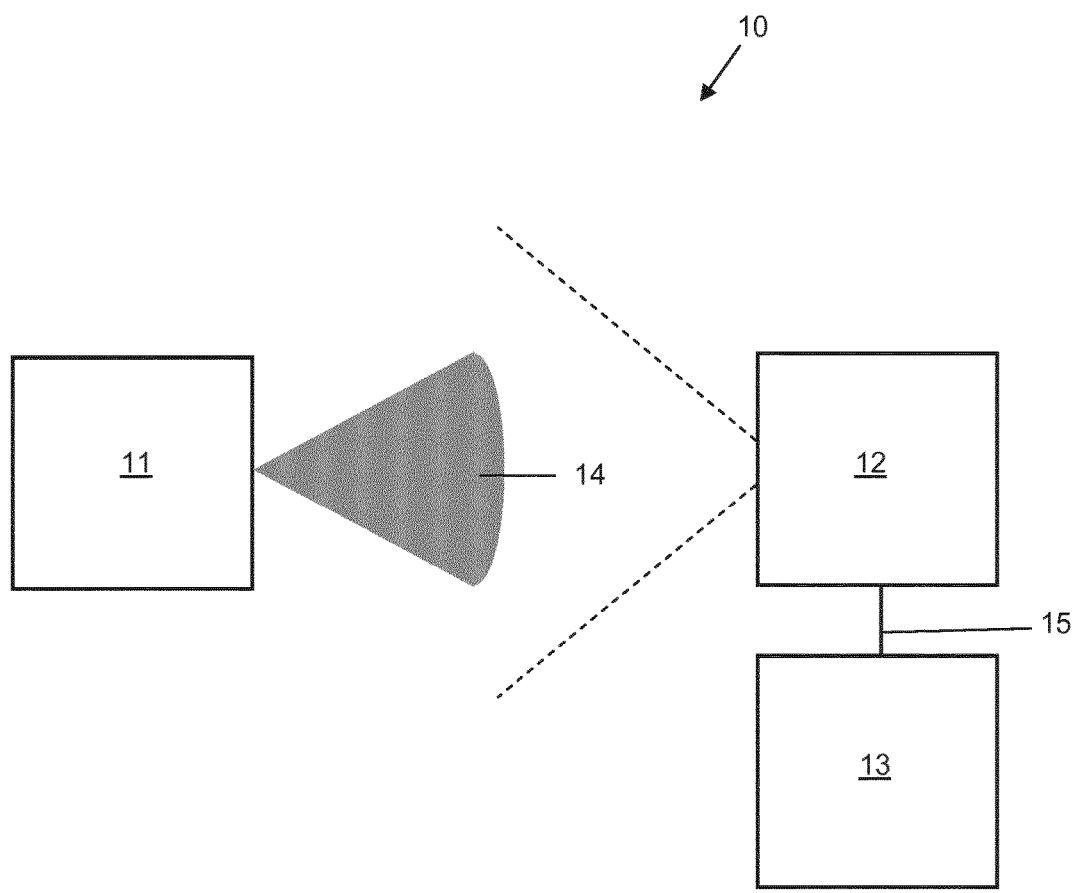
FIG. 1 is an illustration of an example apparatus for detecting when a subject has exited an item of furniture, according to a general embodiment of the invention.

FIG. 1 shows an apparatus 10 for detecting when a subject has exited an item of furniture, according to a general embodiment. The apparatus comprises a light source 11 arranged to emit light 14, a camera 12, and a processing unit 13.

The phrase "processing unit" is used herein to refer to an entity or system for processing, for example, those that process in response to a signal or data and/or those that process autonomously. A processing unit should be understood to encompass microprocessors, microcontrollers, programmable digital signal processors, integrated circuits, computer software, computer hardware, electrical circuits, application specific integrated circuits, programmable logic devices, programmable gate arrays, programmable array logic, personal computers, chips, and any other combination of discrete analog, digital, or programmable components, or other devices capable of providing processing functions.

The light source 11 is configured for use underneath an item of furniture which has an upper side for supporting a subject and an underside opposite to the upper side and comprises an overhanging component that extends from the underside toward a surface on which the item of furniture is resting, wherein the overhanging component comprises a proximal edge and a distal edge opposite to the proximal edge, the distal edge being farther from the underside than the proximal edge. The light source 11 is arranged to illuminate an edge-feature associated with the distal edge of the overhanging component of the item of furniture such that a shadow of the edge-feature is created on a region of the surface. In some embodiments the light source 11 is a directional light source. In some embodiments the apparatus 10 comprises multiple light sources. In some such embodiments each of the multiple light sources can be arranged to create a shadow on a different region of a surface on which the item of furniture is resting, or a different surface near to the item of furniture.

In some embodiments the light source 11 is arranged such that substantially all of the light emitted by the light source has a wavelength in a predefined range. Preferably the light source 11 is arranged to emit light at a wavelength at which other light sources in the location where the apparatus is to be used do not emit a signification amount of light, or do not emit light at a high intensity relative to the intensity of light at that wavelength emitted by the light source 11. Advantageously, using a wavelength at which other light sources do not emit much light, or only emit with low intensity, ensures that the shadow will appear as a high-contrast object in images acquired by a camera arranged to preferentially detect light at that wavelength.

In some such embodiments the light source comprises an optical filter arranged to permit passage of light having a wavelength in the predefined range. In some embodiments the light source 11 is arranged to emit near-infrared (IR) light. Advantageously, a light source which uses near-IR light can prevent visual disturbance to the subject or hospital staff. Preferably the light source is arranged to emit light at an intensity which is sufficiently high to create a well-defined shadow, even when the apparatus 10 is operating in a well-lit environment. In some embodiments the light source is arranged such that the intensity of the light emitted by the light source is variable, e.g. in response to a control signal from a processing unit (e.g. the processing unit 13) or from a user interface of the light source 11.

In some embodiments the light source 11 is arranged such that the angle between the light source 11 and a surface to which it is attached is adjustable. In some such embodiments the light source 11 comprises a mounting component configured to permit the light source 11 to be attached to a surface at any one of a range of possible mounting angles. Advantageously, such embodiments facilitate optimal positioning of a light source in relation to an edge-feature to be illuminated. Preferably the light source 11 is arranged to be rigidly fixed with respect to the edge-feature to be illuminated, and/or the region of the surface on which the shadow is to be created.

In some embodiments the light source 11 includes a user interface for receiving inputs from a user. In some such embodiments the user interface includes an on/off switch. In some embodiments the user interface includes a function to enable a user to set a parameter (e.g. intensity, wavelength, etc.) of the light emitted by the light source 11. In some embodiments the light source 11 is in communication with a remote processing unit, e.g. by means of a wired or wireless communications link. In some such embodiments the light source 11 is arranged to receive control signals from the remote processing unit. In some embodiments the remote processing unit is the processing unit 13 of the apparatus 10.

The camera 12 is arranged to capture sequential images of the region of the surface. The camera 12 is arranged to detect light of the same type as the light emitted by the light source 11. For example, in embodiments in which the light source 11 is arranged to emit near-IR light, the camera 12 is arranged to detect near-IR light and to generate images based on the detected near-IR light. In embodiments in which the light source 11 is arranged such that substantially all of the light emitted by the light source has a wavelength in a predefined range (e.g. by means of the light source comprising an optical filter), the least one camera is arranged to detect light having a wavelength in the predefined range. In some such embodiments the camera 12 comprises an optical filter arranged to permit the passage of light having a wavelength in the predefined range and to block the passage of light having a wavelength outside of the predefined range.

In some embodiments the camera 12 is a 2D camera. In some embodiments the camera 12 is a wide-angle camera. In some embodiments the apparatus 10 comprises a plurality of cameras, in which case the images from each camera may be stitched together by the processing unit 13, to create a single large image, before being analyzed to detect shadows, etc. In situations in which it is desired to monitor two or more sides of an item of furniture simultaneously, providing multiple cameras can enable a surface at each side of the item of furniture to be within the captured images without needing the subject-supporting surface of the item of furniture to be within any of the captured images. Privacy of a subject occupying the item of furniture can therefore be maintained.

The camera 12 has a field of view (FOV), represented by the dashed lines in FIG. 1, which is preferably wide enough to encompass at least one shadow created by illumination of an edge-feature when the light source(s) 11 and the camera 12 are positioned for use. In some embodiments the camera 12 is a video camera, which is arranged to capture a video stream comprising a plurality of consecutive video frames. In some embodiments the camera is a still camera, arranged to capture a series of still images, e.g. during a recording period.

The processing unit 13 is arranged to receive the images from the camera 12, e.g. via a communications link 15. The communications link 15 may be wired or wireless. The processing unit 13 is further arranged to detect the edge of the shadow in each of the received images. The shape of the shadow will depend on the configuration of the illuminated edge-feature. For example, where the illuminated edge-feature comprises a straight edge, the shadow of the edge-feature will comprise a dark area in each received image, which is bounded on one side by a straight edge corresponding to the straight edge of the illuminated edge-feature. An embodiment in which the illuminated edge-feature comprises a straight edge is illustrated in FIGS. 2a and 2b.

Figure 2A:
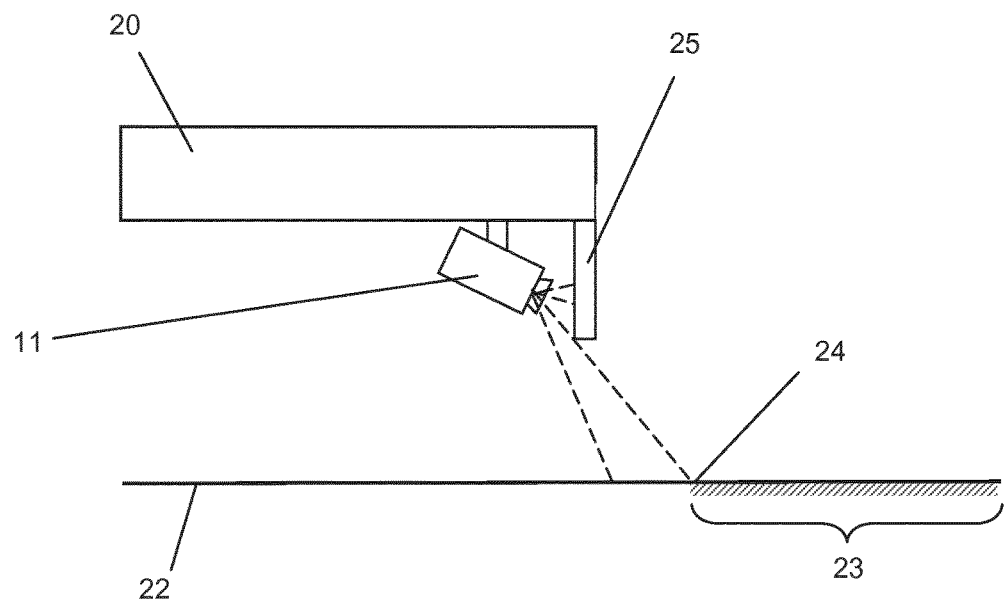
FIG. 2a shows a light source of the example apparatus of FIG. 1, in use to illuminate an edge-feature associated with the lower edge of the overhanging component of a bed.
Figure 2B:
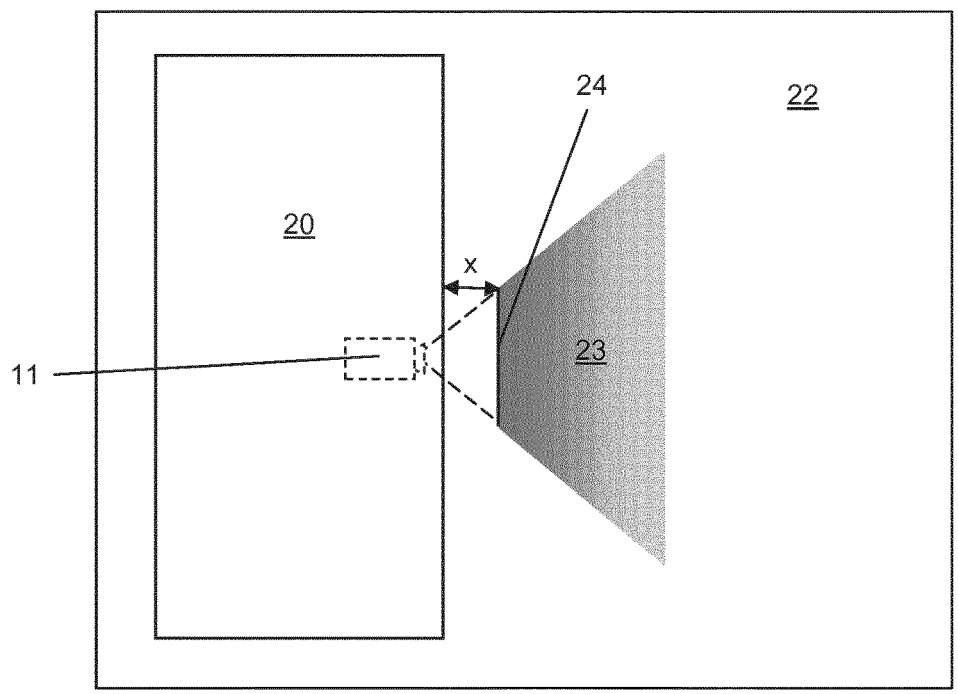

FIG. 2a shows a cross section through part of a bed 20 to which a light source 11 of an apparatus 10 is attached. FIG. 2b shows a plan view of the bed 20 and the surrounding floor 22. The bed 20 has an overhanging component 25 which extends from an underside of the bed 20 towards the floor 22 on which the bed 20 is resting. The overhanging component 25 comprises an upper edge and a lower edge opposite to the upper edge. The lower edge is farther from the underside of the bed 20 than the upper edge, which as it can be seen in FIG. 2a is connected to the underside. Thus, the upper edge is a proximal edge and the lower edge is a distal edge. The lower edge (i.e., the distal edge) of the component 25 comprises an edge-feature associated with the underside of the bed 20. The light source 11 is attached to the underside of the bed 20 and is directed such that some of the light emitted by the light source 11 is incident on the floor 22 in a region adjacent the bed 20, and some of the light emitted by the light source 11 is incident on the overhanging component 25 (i.e. the overhanging component 25 blocks some of the light emitted by the light source 11).

As a result of the blocking of some of the emitted light by the overhanging component 25, a shadow 23 is created on the floor 22, at a distance x from the side of the bed. The edge 24 of the shadow 23 which corresponds to the lower edge of the overhanging component 25 is straight (as can be seen in FIG. 2b), because the lower edge of the overhanging component is straight. It will be appreciated that if the lower edge of the overhanging component was not straight (e.g. if it was curved, stepped, crenellated, sawtooth, etc., the shadow edge 24 would correspondingly not be straight (i.e. a curved edge of the overhanging component would create a curved shadow edge, etc.). Throughout the rest of the specification, the term "shadow edge" will be used to refer to an edge of a shadow which corresponds, in the manner described above, to the illuminated edge-feature (i.e. the physical edge) which casts the shadow. A shadow of an edge-feature, created on a surface by illumination of that edge-feature, is therefore a shadow edge.

The processing unit 13 may be arranged to use any suitable edge detection algorithm(s) known in the art to detect the shadow edge in the received images. In some embodiments, e.g. embodiments in which the apparatus 10 comprises at least one camera 12 (e.g. arranged to view multiple sides of an item of furniture) and multiple light sources 11 (e.g. arranged to illuminate different edge-features associated with an underside of the item of furniture), the processing unit 13 is arranged to detect multiple shadow edges in each of the received images. Advantageously, in such embodiments the apparatus 10 can monitor several sides of an item of furniture simultaneously. In preferred embodiments, the intensity of the light emitted by the light source 11 is high compared to the intensity of background light having the same wavelength. This advantageously ensures that the shadow will appear as a high-contrast object in the images generated by a camera arranged to preferentially detect light having the same wavelength as the light emitted by the light source, and also that the shadow edge 24 is well-defined. A well-defined, high-contrast object in an image is straightforward to detect using simple image processing techniques, and consequently the computational resource required for detecting the shadow edge is low compared to what would be required, e.g., for detecting a subject on the bed.

The processing unit 13 is further arranged to detect, in the received images, the appearance of a feature contiguous with a detected shadow edge. A feature may comprise, for example, a local deformation of the shadow edge, an additional shadow touching or overlapping the shadow edge, an object touching or overlapping the shadow edge, etc. In some embodiments the processing unit is arranged to detect features which appear at the bed (i.e. lit) side of the shadow edge and is not arranged to detect features which appear at the opposite side (i.e. within the shadow). In embodiments in which the processing unit 13 is arranged to detect multiple shadow edges (e.g. when multiple sides of an item of furniture are being monitored by a single apparatus 10), the processing unit 13 is arranged to separately and simultaneously detect the appearance of a feature contiguous with a detected shadow edge in respect of each shadow edge detected in the received images.

In some embodiments the processing unit 13 is arranged to detect the appearance of a feature contiguous with a detected shadow edge by comparing a first image (which may, in some embodiments, comprise a video frame) acquired at a first time, to a second image (which may, in some embodiments, comprise a video frame) acquired at a second, later, time. The second time may be immediately (as far as is possible with regards to how frequently the camera 12 is arranged to acquire images/video frames) after the first time, or alternatively may be a predetermined length of time after the first time. In some such embodiments, if a feature contiguous with the shadow edge is present in the second image but is not present in the first image, the processing unit is arranged to determine that a feature has appeared contiguous with the shadow edge. In some embodiments the processing unit 13 is arranged to perform such a comparison in respect of each consecutive (in time) pair of received images.

The processing unit 13 is further arranged to monitor how a detected feature (i.e. a feature which has appeared contiguous with a shadow edge) changes over a time period. In some embodiments the processing unit is arranged to monitor changes to a detected feature over a time period by determining a first value for a property of the feature in a first image acquired at a first time; determining a second value for the property of the feature in a second image acquired at a second, later, time; and comparing the second value to the first value. The property of the feature can be, e.g., size of the feature, area of the feature, shape of the feature, location of the feature; extension of the feature perpendicular to the shadow edge, etc. In some embodiments the processing unit 13 is arranged to determine a rate of change of the detected feature over the time period, based on the first value, the second value, the acquisition time of the first image, and the acquisition time of the second image. In some embodiments the processing unit is arranged to monitor changes to a detected feature over a time period by determining a direction of motion of the detected feature over the time period.

Figure 5:
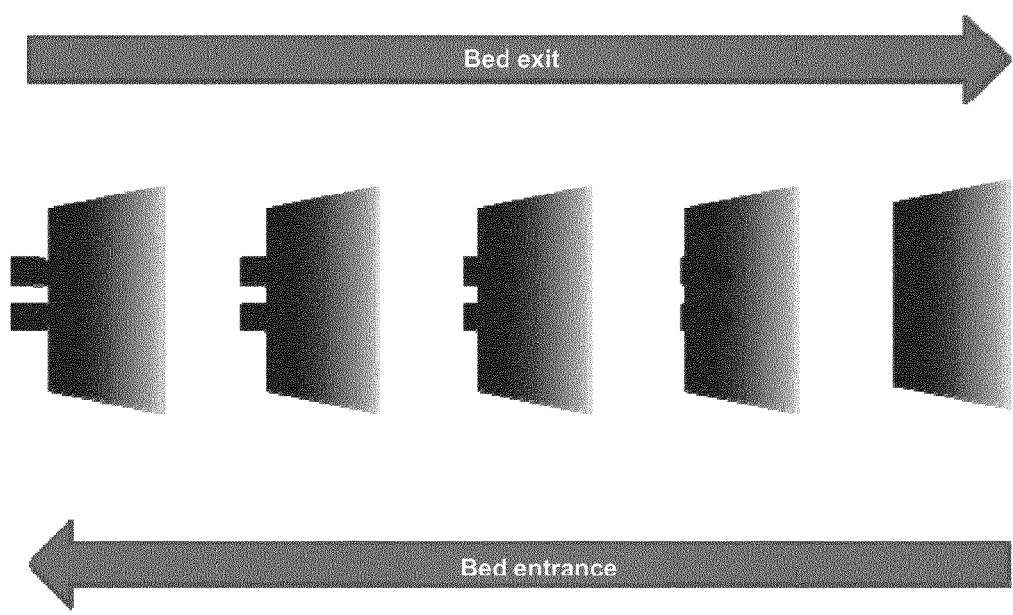
FIG. 5 shows an example series of images representing a subject exit event, according to an embodiment of the invention.

FIG. 5 shows, if read from left to right, an example set of images representing a bed exit event (or, if read from right to left, a bed entry event). In the first (i.e. far left) image two deformations of the shadow edge have appeared, corresponding to the feet of a subject. The deformations have the form of protrusions extending from the shadow edge in the direction of the bed. In subsequent images each protrusion becomes smaller (i.e. the extension of each protrusion perpendicular to the shadow edge decreases, and so does the area of each protrusion. In an example embodiment of the apparatus 10, the processing unit is arranged to detect the protrusions as features which have appeared contiguous with the shadow edge, and to monitor changes to the detected features by determining an extension of each protrusion in each successive image, and comparing extension values between pairs of consecutive images.

In some embodiments the time period over which the processing unit is arranged to monitor changes to a detected feature comprises a time period for which the feature is present in the received images. For example, in the scenario shown in FIG. 5, the time period begins with the far left image, which is the earliest acquired image in which the protrusions were present, and ends with the second rightmost image, which is the latest image in which the protrusions were present. In such embodiments the processing unit 13 can determine a duration of the time period by comparing the acquisition time of the earliest acquired image in which the protrusions were present to the acquisition time of the latest acquired image in which the protrusions were present. In some embodiments the time period over which the processing unit is arranged to monitor changes to a detected feature comprises a time period having a fixed length, which begins with the earliest acquired image in which the detected feature is present.

In some embodiments the processing unit is arranged to generate a change signal based on a time series of values, e.g. feature property values, difference values, etc. The processing unit 13 can be arranged to use any suitable known signal analysis and feature extraction techniques in the detection and monitoring of features in the received images.

The processing unit 13 is further arranged to determine whether a change to a detected feature satisfies at least one predefined criterion for a subject exit event. In some embodiments the predefined criterion comprises a set of one or more conditions. In some embodiments the at least one predefined criterion for a subject exit event comprises a threshold (e.g. a minimum threshold) for a change to a given property of a detected feature over a time period. In some embodiments the at least one predefined criterion for a subject exit event comprises a condition specifying a direction of change (e.g. increase, decrease) of a detected feature over a time period. In some embodiments the at least one predefined criterion for a subject exit event comprises a condition relating to the direction of motion of a detected feature. In some embodiments the at least one predefined criterion for a subject exit event comprises a condition relating to the shape of a change signal. Conditions relating to the shape of a change signal can comprise any or all of: a measure of the variability of a change signal, an amount of time for which the variability of a change signal exceeds a predefined threshold, relative locations of peaks in a change signal, relative heights of peaks in a change signal, area under a change signal, frequency of periods when a change signal exceeds a predefined threshold, etc.

In some embodiments the predefined criterion for a subject exit event is defined such that motion of a detected feature in a direction toward the shadow edge (i.e. the detected shadow edge which the feature appeared contiguous with) during the time period will be determined by the processing unit to satisfy the predefined criterion and motion of a detected feature in a direction away from the shadow edge will be determined by the processing unit not to satisfy the predefined criterion. In some such embodiments the processing unit 13 is arranged to determine that a direction of motion of a detected feature is away from the detected shadow if a distance between a given part of the feature and the detected shadow increases, on average, over a predefined time period (e.g. 1 minute) after the feature was first detected contiguous with the shadow.

In some embodiments the processing unit 13 comprises or is in communication with a memory storing a set of predefined change signatures corresponding to various different types of bed exit event (e.g. falling out of bed, sitting up and then getting out of bed, lowering the legs onto the floor from a prone position, etc.). A change signature may comprise, e.g., one or more change signals and/or sets of conditions relating to changes in one or more properties of a feature, of any of the types described above. In some such embodiments the at least one criterion comprises a change signature, and determining whether a change to a detected feature satisfies the at least one predefined criterion comprises determining whether a change signal generated for the detected feature matches the change signature. In some embodiments the processing unit 13 is further arranged to calculate confidence information in respect of each determination of whether a change to a detected feature satisfies at least one predefined criterion for a subject exit event.

In some embodiments the predefined criterion for a subject exit event is defined such that changes to features representing persons or items other than the subject would not satisfy a predefined subject entry criterion For instance, a condition requiring a minimum rate of change can be included in the predefined criterion to exclude shadows created by inanimate objects. In some embodiments the processing unit is provided with a set of predefined "other person" change signatures corresponding to various different movement patterns commonly exhibited by persons other than the subject (e.g. caregivers, cleaners, family members). In some such embodiments the predefined criterion for a subject exit event is defined such that a change signal generated for the detected feature which matches one of the "other person" change signatures is determined not to satisfy the predefined criterion.

The processing unit 13 is further arranged to output a signal based on the determining. In some embodiments the signal comprises a control signal, e.g. to a device having a wired or wireless communications link with the processing unit 13. Such a device could be, e.g., a communications device, a display device, an alarm device, etc. In such embodiments the control signal may be arranged, for example, to cause one or more of:
  an alarm device (e.g. a visual or audio alarm generating device) to generate an alarm;
  a communications device to generate a message to a caregiver;

a communications device to generate a message to the subject;

a communications device to send a signal to a remote device (e.g. a pager, PDA or mobile phone of a medical professional);

a display device (e.g. a monitor or screen) to display information.

In some embodiments the signal comprises a message to a caregiver, e.g. indicating that a bed exit event has been detected. In some embodiments the signal comprises a message to the subject, e.g., to instruct them to remain in bed until assistance arrives. In some embodiments the processing unit is arranged to output a plurality of signals, for example a communications signal to a communications device such as a mobile phone of a medical professional, and a control signal to an alarm device causing it to generate an alarm.

In some embodiments in which the apparatus 10 comprises multiple light sources, each of the multiple light sources is for use underneath the same item of furniture. However; each of the multiple light sources is arranged to illuminate a different edge-feature, e.g. a first edge-feature associated with a first side of the item of furniture and a second edge-feature associated with a second, different side of the item of furniture. The resulting shadows are therefore created adjacent to different sides of the item of furniture. In some embodiments the resulting shadows are created adjacent to opposite sides of the item of furniture. In some embodiments the resulting shadows are created adjacent each side of the item of furniture from which it is possible for a subject to exit the item of furniture. Advantageously, embodiments which utilize multiple projectors to project patterns on different sides of the item of furniture enable every side of an item of furniture from which a subject could exit the item of furniture to be monitored, ensuring that an exit event is not missed by the apparatus 10. Such embodiments therefore have a high detection sensitivity.

For example, in one such embodiment a first directional light source is fixed to a bed base such that it emits light toward a first side of the bed, and a second directional light source is fixed to the bed base in a similar location, but positioned to emit light in the opposite direction to the first light source. The first light source illuminates a first overhanging part of the bed frame which extends towards the floor on which the bed is resting along a first long side of the bed. The second light source illuminates a second overhanging part of the bed frame which extends towards the floor along a second long side of the bed, which is opposite to the first long side. Consequently, a first shadow is created on a surface (e.g. the floor or a wall) adjacent the first long side of the bed, and a second shadow is created on a surface (e.g. the floor or a wall) adjacent the second long side. In such embodiments the camera is positioned such that both shadows are within its FOV, and the processing unit 13 is arranged to detect two shadows in each of the received images. In some such embodiments the processing unit 13 is arranged to detect the appearance of a feature contiguous with the first shadow edge and to detect the appearance of a feature contiguous with the second shadow edge. The motion of a detected feature is then analyzed by the processing unit 13 in the same manner, regardless of which shadow edge it appeared contiguous with.

In some embodiments in which the apparatus 10 comprises multiple light sources, each of the multiple light sources is for use underneath the same item of furniture and is arranged to illuminate the same edge-feature associated with a distal edge of an overhanging component of the item of furniture. The resulting shadows are therefore created adjacent to the same side of the item of furniture. If each of the multiple light sources is arranged at the same distance from the illuminated edge-feature, and at the same angle with respect to the illuminated edge-feature and the surface, then each of the multiple shadows will be created on the surface at the same distance from the item of furniture. The light sources can be arranged such that the shadows overlap to create an overall shadow which is larger than the shadows which would be individually cast by each light source 11. Advantageously, such embodiments enable an overall shadow to be created which extends along an entire side of an item of furniture; regardless of how large the item of furniture is, ensuring that a subject cannot exit the item of furniture from that side without crossing the shadow. Such embodiments are therefore especially suitable for use with large items of furniture such as hospital beds. In such embodiments the camera 12 is preferably for positioning such that all or most of the overall shadow is within its FOV, and the processing unit is preferably arranged to detect the overall shadow in the received images as if it were an individual shadow.

In some embodiments the apparatus 10 is additionally for detecting when a subject has entered an item of furniture. In such embodiments the processing unit 13 is further arranged to determine whether a change to a detected feature over the time period satisfies at least one predefined criterion for a subject entry event. The at least one predefined criterion for a subject entry event may have any of the features described above in relation to the at least one criterion for a subject exit event. However; it will be appreciated that a subject entry event will typically involve changes (e.g. of feature properties) in the opposite direction to a subject exit event. For example, the property of feature area is expected to decrease during a subject exit event (as shown by FIG. 5) and is expected to increase during a subject entry event.

In some embodiments the predefined criterion for a subject entry event is defined such that motion of a detected feature over the time period in a direction toward the shadow edge will be determined by the processing unit not to satisfy the predefined criterion. In some embodiments the predefined criterion for a subject entry event is defined such that changes to features representing persons or items other than the subject would not satisfy a predefined subject entry criterion (this can be achieved, e.g. in a similar manner to that discussed above in relation to the predefined criterion for a subject exit event). In some embodiments the processing unit 13 is further arranged to calculate confidence information in respect of each determination of whether a change to a detected feature satisfies at least one predefined criterion for a subject entry event. In embodiments for detecting subject entry events the processing unit 13 is further arranged to output a signal based on the determining of whether a change to a detected feature satisfies at least one predefined criterion for a subject entry event.

Figure 3:
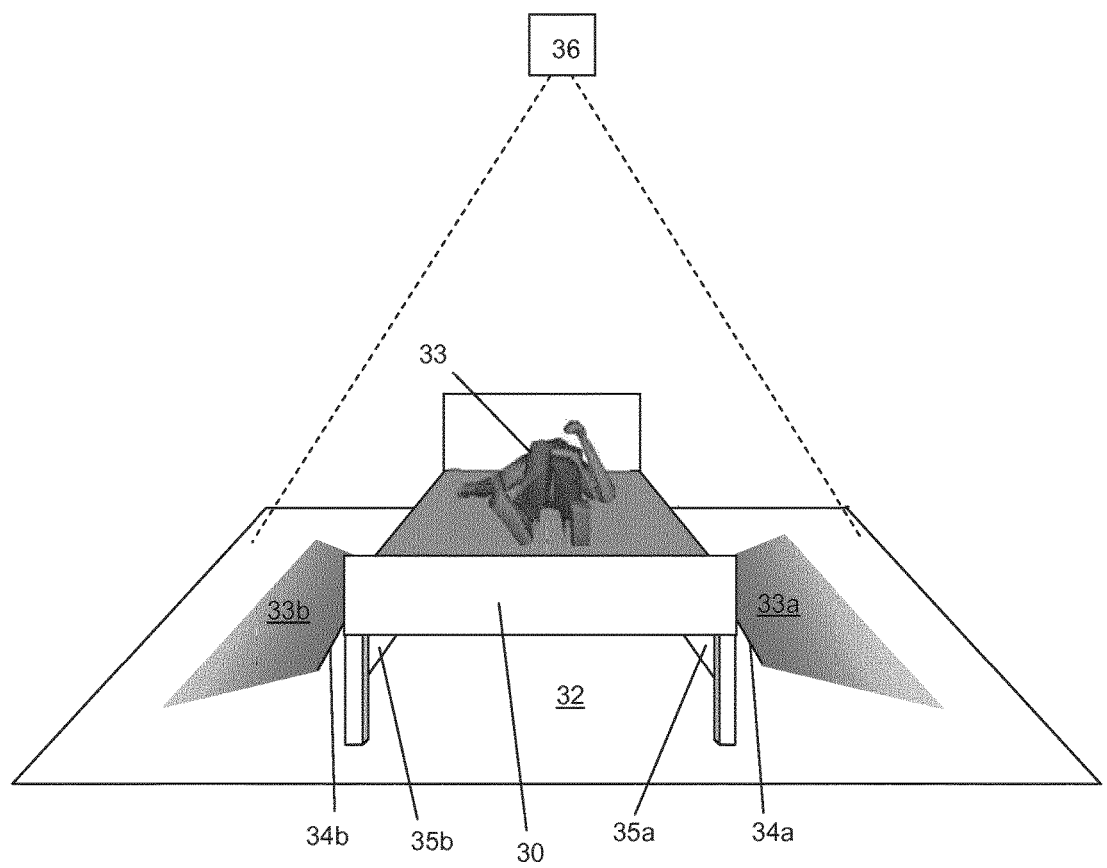
FIG. 3 shows an example apparatus according to an embodiment of the invention, in use with a bed.

FIG. 3 shows the apparatus of FIG. 1 in use with an item of furniture. In the illustrated example the item of furniture comprises a hospital bed 30 having, along each long side, an overhanging component 35a, 35b which extends from an underside of the bed toward the floor 32 on which the bed is resting. However; in other examples the item of furniture can comprise another type of bed, a chair, a wheel chair, or any item of furniture which can be occupied by a subject. It will be appreciated that certain items of furniture for which it could be desirable to monitor subject exit events may not comprise components having edge-features suitable for creating a shadow on a surface when illuminated by a light source arranged under the item of furniture. The apparatus 10 can be used in conjunction with such items of furniture by providing an edge member for attachment to the item of furniture (e.g. by any suitable known attachment mechanism). In some such embodiments the edge member is removably attachable to the item of furniture. In some embodiments an edge member comprises a linear protrusion which, when attached to an item of furniture, extends from the underside of the item of furniture toward a surface on which the item of furniture is resting. In some embodiments the overhanging components 35a, 35b of FIG. 3 comprise edge members removably attached to the hospital bed 30.

Two light sources (not visible in FIG. 3) are arranged beneath the hospital bed in opposite orientations, to respectively illuminate the overhanging component 35a and the overhanging component 35b. The light sources are preferably arranged such that the shadows 33a, 33b are created at a suitable distance from the long sides of the bed 30, such that a subject exiting the bed must cross one of the shadow edges 24. In the example of FIG. 3, the light sources are attached to the base of the bed 30, e.g. by a mounting bracket. In other embodiments the light source(s) are not attached to the item of furniture. Instead, the light source(s) can be supported on the floor underneath the item of furniture (e.g. by a stand or tripod). In the example of FIG. 3, two oppositely directed light sources are used because a subject may exit the bed 30 from either long side of the bed. It will be appreciated, however, that if the bed 30 was arranged with one of the long sides against a wall such that a subject could not get exit the bed on that side, it would only be necessary to provide one or more light sources directed toward the other long side of the bed (i.e. the long side not against a wall).

When setting up the apparatus 10 with a particular item of furniture, decisions such as whether to attach the light source to the item of furniture, what angle to position the light source at with respect to the edge-feature to be illuminated, what height to position the light source at, etc., will be taken (e.g. by an engineer installing the apparatus 10) based on the exact configuration of the particular item of furniture. For example, many modern hospital beds are supported on complex mechanisms (e.g. for raising and lowering and/or changing the angle of the subject support surface) and when installing an apparatus 10 to monitor such a hospital bed, it will be necessary to ensure that the light emitted by the light source 11 is not obscured by any parts of the bed support mechanism. Preferably the light source (or multiple light sources) is positioned such that the shadow edge(s) extend along most or all of a side of the item of furniture from which a subject might exit that item of furniture.

Figure 4A:
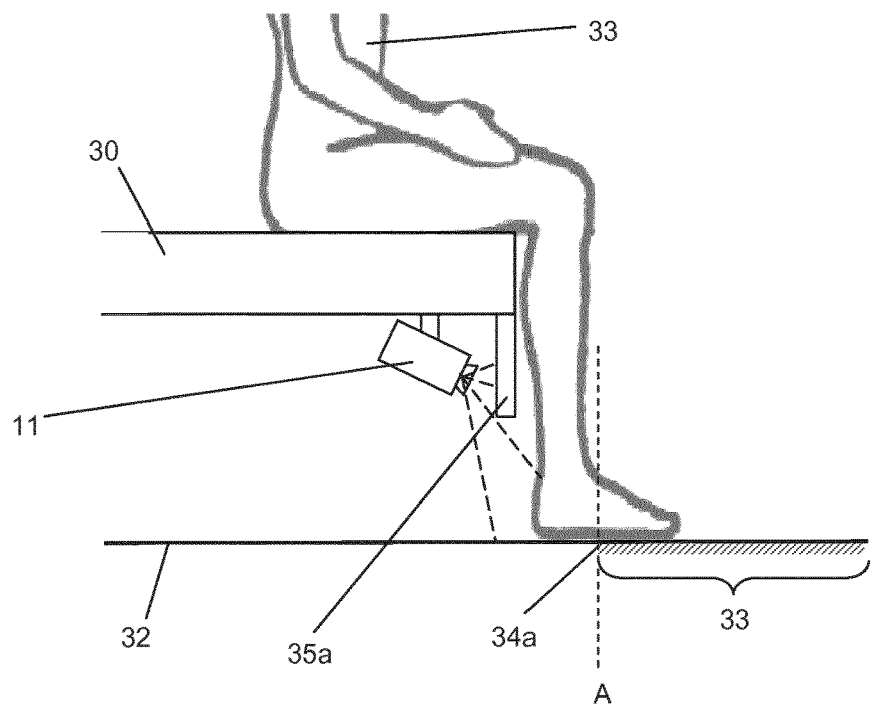
FIG. 4a shows part of the example apparatus of FIG. 3, during a subject exit event.
Figure 4B:
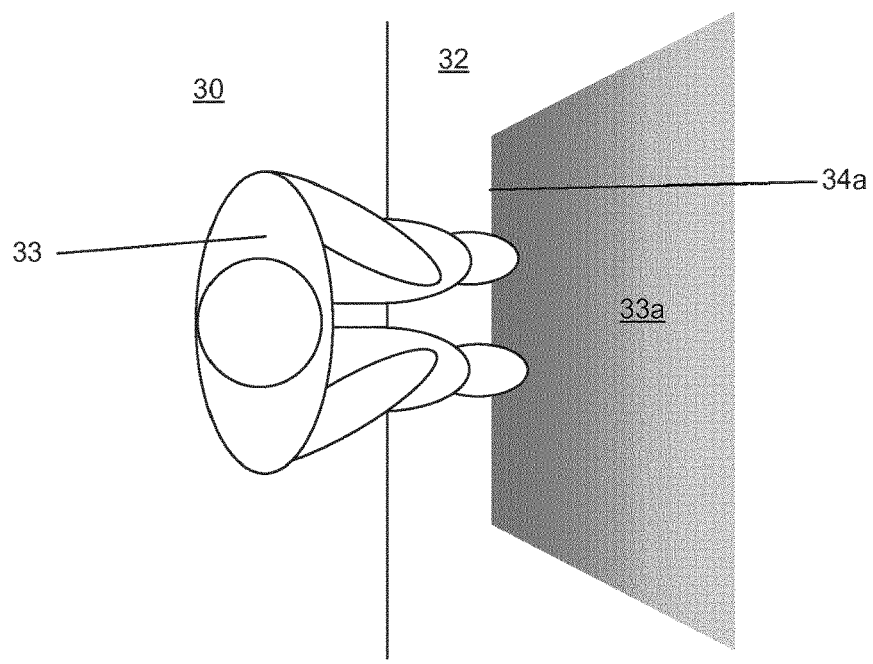

When the subject 33 moves a part of their body over one of the long edges of the bed 30 and onto the floor 32 adjacent the bed, e.g. as part of a bed exit movement, that body part will block some of the light emitted by the light source directed toward that edge of the bed, as illustrated by FIG. 4. The dashed line A in FIG. 4a shows the location of the shadow edge 34a. It can therefore be seen that the subject's feet cross this shadow edge. Consequently, when the subject is in the position shown in FIG. 4a, the shadow edge in the images acquired by the camera 12 will include two local deformations corresponding to each of the subject's feet. FIG. 4b shows part of an example image acquired by the camera 12 of the situation shown in FIG. 4a. As the subject completes the bed exiting movement and moves away from the bed they will move fully into the shadow, such that no part of their body is blocking the light emitted by the light source.

This movement is represented in the received images as the local deformations shrinking toward the shadow edge 34a and eventually disappearing. This process is illustrated by FIG. 5, which if read from left to right shows an example set of images representing a bed exit event. It will be appreciated that a bed entry event would appear, in the received images, like a reversal of a bed exit event (i.e. one or more small local deformations of the shadow edge would appear, and would subsequently grow away from the shadow edge).

In some embodiments the light sources are manually activated, e.g. by person activating an on-switch of each light source, and emit light continually until manually deactivated, e.g. by a person activating an off-switch. In some embodiments the light sources are automatically activated, e.g. by a control signal from a processing unit. In some embodiments the light sources have a communications link with the processing unit 13 and each light source activated (and subsequently deactivated) by a control signal from the processing unit 13. Preferably the light sources are only activated during times when the item of furniture is in use. For the purposes of the invention, an item of furniture is considered to remain "in use" during temporary absences of a subject using the item of furniture, e.g. to visit the bathroom, or to undergo treatment. By contrast, an item of furniture is considered to be not in use during the period between the discharge of a subject who was previously occupying that item of furniture, and the first occupation of that item of furniture by a new subject.

In the example of FIG. 3 the camera 12 and the processing unit 13 are integrated into a monitoring device 36. The monitoring device 36 is positioned centrally above the bed 30, such that both of the shadows 33a and 33b are within the FOV of the camera 12 (represented by the dashed lines in FIG. 3).

In use of the apparatus 10, the light sources are activated in one of the manners described above such that they continually illuminate the edges of the overhanging components 35a, 35b, which thereby respectively create shadows 33a, 33b on the floor 32. The camera 12 captures images of the floor 32, which include the shadows 33a, 33b and shadow edges 34a, 34b during a recording period. In some embodiments the camera continually captures images during the whole time the apparatus 10 is in use, such that the recording period comprises the period for which the apparatus 10 is in use. In some embodiments the camera is activated in response to an event. In some such embodiments the event comprises a detection of motion of the subject by a separate motion detector (e.g. an accelerometer attached to the item of furniture, or a separate camera-based motion detection system). In some embodiments the camera is arranged to capture images for a predefined amount of time (i.e. the duration of the recording period is predefined). In some embodiments the captured images comprise video frames. In some embodiments the camera captures a series of still images.

Images captured by the camera are sent to the processing unit 13. The processing unit 13 continually assesses, on the basis of the captured images, whether a subject exit event is occurring (or has occurred), e.g. by performing the method shown in FIG. 6. In some embodiments the processing unit 13 additionally continually assess, on the basis of the captured images, whether a subject entry event is occurring (or has occurred), e.g. by performing the method shown in FIG. 6.

Figure 6:
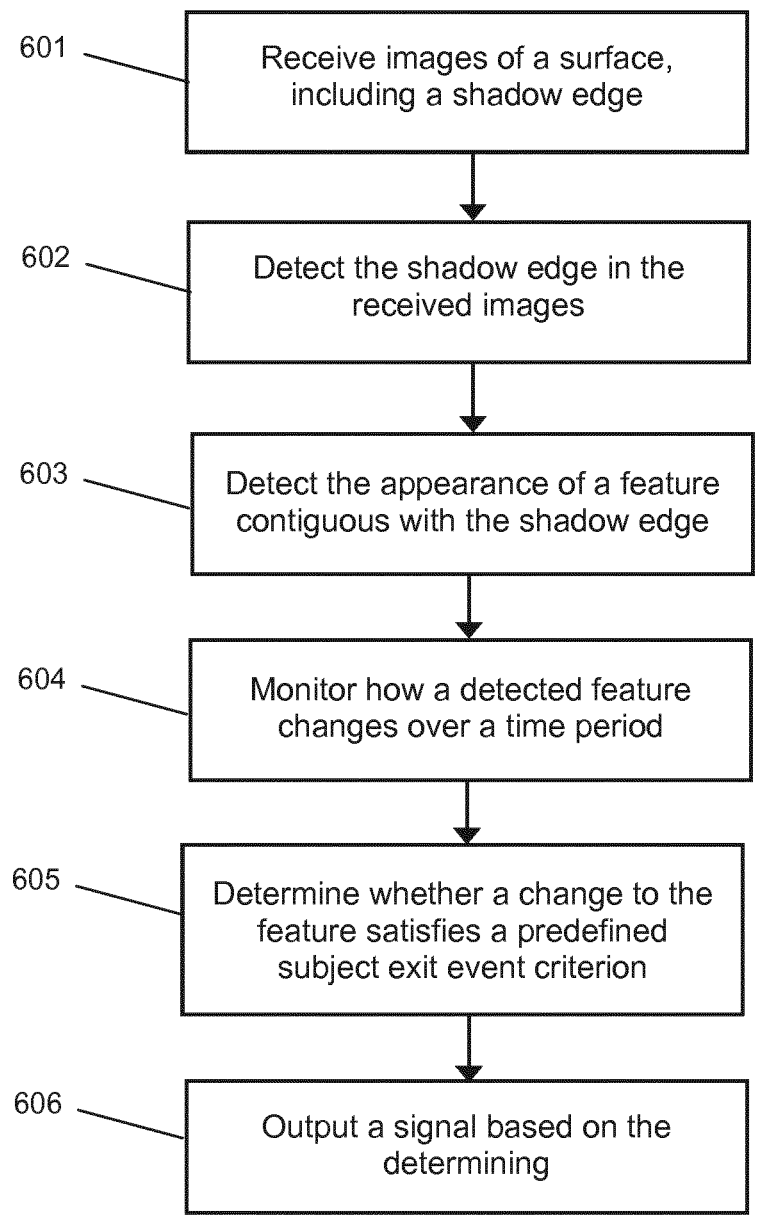
FIG. 6 is a flow chart illustrating a method for detecting when a subject has exited an item of furniture, according to a general embodiment of the invention.

FIG. 6 illustrates a method for detecting when a subject has exited an item of furniture. In a first step, 601, sequential images of a region of a surface (e.g. the floor 32) are received (e.g. by the processing unit 13). Each of the images includes a shadow cast by an edge-feature associated with a distal edge of an overhanging component of an item of furniture (e.g. the bed 30). The item of furniture has an upper side for supporting a subject, and the underside is opposite to the upper side. In some embodiments the images are received from the camera which captured the images, e.g. via a wired or wireless communication link. In some embodiments the images are received from a remote server (e.g. a central hospital server), e.g. via a wired or wireless communication link. In some embodiments the images are received on a machine-readable non-transitory storage medium. In some embodiments the images are received in real time or near-real time (i.e. as they are captured by a camera). In some embodiments the images are received from multiple sources, e.g. a first camera, arranged to monitor a first item of furniture, and a second camera, arranged to monitor a second item of furniture.

In step 602 an edge of the shadow is detected in the received images, e.g. by the processing unit 13. In some embodiments the shadow edge is detected in the manner described above in relation to the operation of the processing unit 13. In some embodiments performing step 602 comprises detecting the shadow edge in each frame of a received video stream. In some embodiments performing step 602 comprises detecting the shadow edge in each image of a received series of still images.

In step 603, the appearance of a feature contiguous with the shadow edge is detected in the received images, e.g. by the processing unit 13. In some embodiments performing step 603 comprises detecting the appearance of a feature contiguous with the shadow edge in the manner described above in relation to the operation of the processing unit 13. The result of step 603 may be a positive detection (i.e. it is detected that a feature has appeared contiguous with the shadow edge) or a negative detection (i.e. it is detected that no features have appeared contiguous with the shadow edge).

In step 604, how a feature which appeared contiguous with the shadow edge changes over a time period is monitored, e.g. by the processing unit 13. In some embodiments performing step 604 comprises monitoring how a feature which appeared contiguous with the shadow edge changes over a time period in the manner described above in relation to the operation of the processing unit 13. In some embodiments step 604 is performed responsive to the result of step 603 being a positive detection. In some embodiments the monitoring of how a detected feature changes over a time period is updated each time a new image is received.

In step 605, it is determined (e.g. by the processing unit 13) whether a change to a feature which appeared contiguous with the shadow edge satisfies at least one criterion for a subject exit event. In some embodiments performing step 605 comprises determining whether a change to a feature which appeared contiguous with the shadow edge satisfies least one predefined criterion for a subject exit event in the manner described above in relation to the operation of the processing unit 13. In some embodiments step 605 is performed continuously, e.g. each time the change monitoring is updated. In some embodiments the time period comprises a predefined time period, e.g. a time period starting with the detection of the appearance of the feature contiguous with the shadow edge and having a predefined length. The determination generated by step 605 may be recalculated in respect of each newly-received image (or each subsequent frame of a video stream).

In step 606 a signal is output (e.g. by the processing unit 13) based on the determining (i.e. based on the result of step 605). In some embodiments performing step 606 comprises outputting a signal in the manner described above in relation to the operation of the processing unit 13. The signal may be output using a communications functionality of a monitoring device (e.g. the monitoring device 36). In some embodiments the signal is output continuously, in real-time or near-real time. In such embodiments, preferably the delay between the receipt of the images and the output of the signal is less than a few seconds, so that medical staff can react rapidly to a detected subject exit event. In some embodiments the signal contains a result of a determination of whether a detected change satisfies at least one predefined criterion for a subject exit event (e.g. an indication that a subject exit event is likely to be occurring/have occurred, if the criterion is satisfied, or an indication that a subject exit event is not likely to be occurring/have occurred, if the criterion is not satisfied). In some embodiments the signal contains confidence information associated with the result of the determination generated in step 605. In some embodiments step 606 is only performed if the result of step 605 is that the at least one criterion is met. In some embodiments the signal contains time information associated with the result of the determination, e.g. the time period during which the detected change(s) on which the determination was based occurred. In some embodiments the signal contains information about a movement type. In some embodiments, e.g. embodiments in which a single camera is used to monitor multiple items of furniture, the signal contains information identifying an item of furniture with which a particular determination result is associated. In some embodiments performing step 606 comprises emitting multiple signals, each signal relating to a different monitored item of furniture.

In preferred embodiments the method of FIG. 6 is performed continuously during a time period, e.g. a time period for which the apparatus 10 is operational. In some embodiments the method includes an additional step (not shown) of determining whether a change to a detected feature satisfies at least one predefined criterion for a subject entry event. In some embodiments performing this additional step comprises determining whether a change to a feature which appeared spatially separate from the shadow satisfies least one predefined criterion for a subject entry event in the manner described above in relation to the operation of the processing unit 13. In some embodiments this additional step is performed continuously, e.g. each time the change monitoring is updated. The determination generated by the additional step may be recalculated in respect of each newly-received image (or each subsequent frame of a video stream).

In some embodiments in which the method includes the additional step of determining whether a change to a detected feature satisfies at least one predefined criterion for a subject entry event, performing step 606 comprises outputting a signal based on the determining of whether a change to a feature satisfies at least one predefined criterion for a subject entry event. In some such embodiments performing step 606 comprises outputting a signal based on the determining of a change to a feature satisfies at least one predefined criterion for a subject entry event, and on a determining of whether a change to a feature satisfies at least one predefined criterion for a subject exit event.

Embodiments of the invention therefore advantageously enable exit of a subject from an item of furniture to be automatically detected, in a reliable and computationally efficient manner.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. Apparatus for detecting when a subject has exited an item of furniture, the item of furniture having an upper side for supporting a subject and an underside opposite to the upper side and comprising an overhanging component that extends from the underside toward a surface on which the item of furniture is resting, wherein the overhanging component comprises a proximal edge and a distal edge opposite to the proximal edge, the distal edge being farther from the underside than the proximal edge, the apparatus comprising:
   a light source for use underneath an item of furniture, wherein the light source is arranged to illuminate an edge-feature associated with the distal edge of the overhanging component of the item of furniture such that a shadow of the edge-feature is created on a region of the surface;
   at least one camera arranged to capture sequential images of the region of the surface; and
   a processing unit arranged to:
      receive the images from the camera;
      detect an edge of the shadow in each of the received images,
      detect, in the received images, the appearance of a feature contiguous with the shadow edge;
      monitor how a detected feature changes over a time period;
      determine whether a change to the detected feature over the time period satisfies at least one predefined criterion for a subject exit event; and
      output a signal based on the determining.

2. The apparatus of claim 1, wherein the processing unit is arranged to detect the appearance of a feature contiguous with the shadow edge by:
   comparing a first image acquired at a first time, to a second image acquired at a second, later, time; and
   if a feature contiguous with the shadow edge is present in the second image but is not present in the first image, determine that a feature has appeared contiguous with the shadow edge.

3. The apparatus of claim 1, wherein the processing unit is arranged to monitor changes to a detected feature over a time period by:
   determining a first value for a property of the feature in a first image acquired at a first time;
   determining a second value for the property of the feature in a second image acquired at a second, later, time; and
   comparing the second value to the first value.

4. The apparatus of claim 3, wherein the property of the feature is any one of: size of the feature, shape of the feature, location of the feature; extension of the feature perpendicular to the shadow edge.

5. The apparatus of claim 3, wherein the processing unit is arranged to monitor changes to a detected feature over a time period by:
   determining a rate of change of the detected feature over the time period, based on the first value, the second value, the acquisition time of the first image, and the acquisition time of the second image.

6. The apparatus of claim 3, wherein the processing unit is arranged to monitor changes to a detected feature over a time period by determining a direction of motion of the detected feature over the time period; and wherein the at least one predefined criterion for a subject exit event comprises a condition relating to a direction of motion of a detected feature.

7. The apparatus of claim 6, wherein the predefined criterion for a subject exit event is defined such that motion of a detected feature in a direction toward the shadow edge during the time period will be determined by the processing unit to satisfy the predefined criterion and motion of a detected feature in a direction away from the shadow edge will be determined by the processing unit not to satisfy the predefined criterion.

8. The apparatus of claim 6, wherein the apparatus is additionally for detecting when a subject has entered an item of furniture and the processing unit is further arranged to determine whether a change to the detected feature over the time period satisfies at least one predefined criterion for a subject entry event; and wherein the predefined criterion for a subject entry event is defined such that motion of a detected feature over the time period in a direction toward the shadow edge will be determined by the processing unit not to satisfy the predefined criterion.

9. The apparatus of claim 1, further comprising an additional light source for use underneath the item of furniture, the item of furniture comprising an additional overhanging component that extends from the underside toward the surface on which the item of furniture is resting, wherein the additional overhanging component comprises a proximal edge and a distal edge opposite to the proximal edge, wherein the distal edge is farther from the underside than the proximal edge;
   wherein the light source and the additional light source are both for use underneath the same item of furniture;
   wherein the light source is arranged to illuminate a first edge-feature associated with the distal edge of the overhanging component of the item of furniture such that first a shadow is created on a first region of the surface and the additional light source is arranged to illuminate a second edge-feature associated with the distal edge of the additional overhanging component of the item of furniture such that a second shadow is created on a second region of the surface; the first region being adjacent a first side of the item of furniture, and the second region being adjacent a second, different, side of the item of furniture;

wherein the at least one camera is arranged to capture sequential images, each of which includes the first region and the second region; and wherein the processing unit is arranged to:

detect an edge of the shadow in each of the received images by detecting an edge of the first shadow and an edge of the second shadow in each of the received images, and detect, in the received images, the appearance of a feature contiguous with the shadow edge by detecting the appearance of a feature contiguous with the first shadow edge and detecting the appearance of a feature contiguous with the second shadow edge.

10. The apparatus of claim 1, wherein the light source is arranged to emit near-infrared light and the at least one camera is arranged to detect near-infrared light.

11. The apparatus of claim 1, wherein the light source is arranged such that substantially all of the light emitted by the light source has a wavelength in a predefined range, and the least one camera comprises an optical filter arranged to permit the passage of light having a wavelength in the predefined range and to block the passage of light having a wavelength outside of the predefined range.

12. A system for detecting when a subject has exited an item of furniture, the system comprising:

an item of furniture having an upper side for supporting a subject and an underside opposite to the upper side and comprising an overhanging component that extends from the underside toward a surface on which the item of furniture is resting, wherein the overhanging component comprises a proximal edge and a distal edge opposite to the proximal edge, the distal edge being farther from the underside than the proximal edge, the item of furniture further having an edge-feature associated with the distal edge of the overhanging component;

a light source arranged to illuminate the edge-feature associated with the distal edge of the overhanging component of the item of furniture such that a shadow of the edge-feature is created on a region of the surface;

a camera arranged to capture sequential images of the region of the surface; and a processing unit arranged to:

receive the images from the camera;

detect an edge of the shadow of the edge-feature in each of the received images, detect, in the received images, the appearance of a feature contiguous with the shadow edge;

monitor how a detected feature changes over a time period;

determine whether a change to the detected feature over the time period satisfies at least one predefined criterion for a subject exit event; and output a signal based on the determining.

13. The system of claim 12, wherein the overhanging component is comprised in an edge member removably attached to the item of furniture.

14. The system of claim 13, wherein the edge member comprises a linear protrusion which, when attached to the item of furniture, extends from the underside of the item of furniture toward the surface on which the item of furniture is resting.

15. A method for detecting when a subject has exited an item of furniture, the item of furniture having an upper side for supporting a subject and an underside opposite to the upper side and comprising an overhanging component that extends from the underside toward a surface on which the item of furniture is resting, wherein the overhanging component comprises a proximal edge and a distal edge opposite to the proximal edge, the distal edge being farther from the underside than the proximal edge, the method comprising:

receiving sequential images of a region of the surface, each of the images including a shadow cast by an edge-feature associated with the distal edge of the overhanging component of the item of furniture;

detecting an edge of the shadow in each of the received images, detecting, in the received images, the appearance of a feature contiguous with the shadow edge;

monitoring how a detected feature changes over a time period;

determining whether a change to the detected feature over the time period satisfies at least one predefined criterion for a subject exit event; and outputting a signal based on the determining.

* * * * *